United States Patent
Cheng

(10) Patent No.: US 8,468,628 B1
(45) Date of Patent: Jun. 25, 2013

(54) PILLOW WITH A CAVITY INTO WHICH A PERSON'S FACE IS PLACED, THE CAVITY HAVING AIR CHANNELS TO FACILITATE BREATHING AND SCENTS ABSORBED INTO A SPONGE, WHICH SCENTS ARE BLOWN INTO THE CAVITY BY A FAN

(71) Applicant: Tom Kwok-Yung Cheng, Rowland Heights, CA (US)

(72) Inventor: Tom Kwok-Yung Cheng, Rowland Heights, CA (US)

(73) Assignee: International Media Enterprise, City of Industry, CA (US)

( * ) Notice: Subject to any disclaimer, the term of this patent is extended or adjusted under 35 U.S.C. 154(b) by 0 days.

(21) Appl. No.: 13/658,096

(22) Filed: Oct. 23, 2012

(51) Int. Cl.
*A47G 9/00* (2006.01)
(52) U.S. Cl.
USPC ............. 5/641; 5/632; 5/638; 5/694; 5/652.2; 5/726
(58) Field of Classification Search
USPC ..... 5/632, 636, 638, 639, 641, 694, 724–726, 5/652.1, 652.2
See application file for complete search history.

(56) References Cited

U.S. PATENT DOCUMENTS

| | | | |
|---|---|---|---|
| 5,652,987 A * | 8/1997 | Fujita | 5/726 |
| 6,023,801 A * | 2/2000 | Lamm | 5/636 |
| 6,128,797 A * | 10/2000 | Shaffer | 5/638 |
| 6,230,350 B1 * | 5/2001 | Goldstein | 5/638 |
| 6,336,237 B1 * | 1/2002 | Schmid | 5/726 |
| 6,546,576 B1 * | 4/2003 | Lin | 5/423 |
| 6,745,418 B1 * | 6/2004 | Turner, Jr. | 5/638 |
| 7,195,660 B2 | 3/2007 | Little | |
| 7,543,345 B2 * | 6/2009 | Wilson et al. | 5/638 |
| 7,607,433 B2 | 10/2009 | Silva et al. | |
| 7,802,334 B1 * | 9/2010 | Larios | 5/726 |
| 7,805,787 B2 | 10/2010 | Wallis | |
| 8,006,335 B1 * | 8/2011 | Andermann | 5/638 |
| D656,356 S * | 3/2012 | Cheng | D6/601 |
| 8,127,384 B2 * | 3/2012 | Carlton | 5/655 |
| 2007/0294831 A1 * | 12/2007 | Siekman et al. | 5/653 |
| 2009/0217459 A1 * | 9/2009 | Rudolph | 5/706 |
| 2010/0205743 A1 * | 8/2010 | Harges | 5/638 |
| 2012/0142999 A1 | 6/2012 | Albu et al. | |

FOREIGN PATENT DOCUMENTS

| | | |
|---|---|---|
| CN | 2061408 U | 9/1990 |
| CN | 102551446 A | 7/2012 |
| KR | 101025713 | 3/2011 |

* cited by examiner

*Primary Examiner* — William Kelleher
(74) *Attorney, Agent, or Firm* — Thomas I. Rozsa

(57) ABSTRACT

An innovative pillow which contains openings for a person to place their face as well as side openings which enable air to enter the cavity so that the person can breathe. The device contains a fan which blows air into the cavity of the pillow so that a person can have cooling air while their face is in the pillow. The device can also be impregnated with essential oils such as eucalyptus so that the various beneficial therapeutic effects can be blown into a person's face while they rest their face within the pillow.

20 Claims, 7 Drawing Sheets

PILLOW WITH A CAVITY INTO WHICH A PERSON'S FACE IS PLACED, THE CAVITY HAVING AIR CHANNELS TO FACILITATE BREATHING AND SCENTS ABSORBED INTO A SPONGE, WHICH SCENTS ARE BLOWN INTO THE CAVITY BY A FAN

BACKGROUND OF THE INVENTION

1. Field of the Invention

The present invention relates to the field of relaxation and in particular pillows which enable a person to lay face down into a cavity within the pillow, the cavity including air channels to facilitate breathing.

2. Description of the Prior Art

The following 10 patents and published patent applications are the closest relevant art to the present invention.

1. U.S. Pat. No. 6,128,797 issued to Timothy A. Shaffer on Oct. 10, 2000 for "Face Down Tanning And Massage Pad" (hereafter the "Shaffer patent");

2. U.S. Pat. No. 6,230,350 issued to Allen H. Goldstein on May 15, 2001 for "Head Support Pad With Air Access Conduit" (hereafter the "Goldstein patent");

3. U.S. Pat. No. 6,745,418 issued to David H. Turner, Jr. on Jun. 8, 2004 for "Pillow" (hereafter the "Turner patent");

4. U.S. Pat. No. 7,195,660 issued to Baird M. Little et al. for "Pillow With Air Filter" (hereafter the "Little patent");

5. U.S. Pat. No. 7,607,433 issued to Elizabeth Silva et al. for "Gas Delivery And Monitoring System" (hereafter the "Silva patent");

6. U.S. Pat. No. 7,805,787 issued to Matthew C. Wallis on Oct. 5, 2010 for "Cushion With Scent Cartridge" (hereafter the "Wallis patent");

7. United States Published Patent Application No. 2012/0142999 to Mirela Alina Albu et al. on Jun. 7, 2012 for "Active Pillow System And A Method For Manipulating A Person's Resting Conditions" (hereafter the "Albu Published patent Application");

8. Chinese patent No. CN2061408U issued to Biren Wang on Sep. 5, 1990 for "Breezy Cool Pillow" (hereafter the "Wang Chinese patent");

9. Korean patent No. KR101025713 issued on Mar. 22, 2011 for "A Ventilating Pillow" (hereafter the "Korean patent");

10. Chinese patent No. CN102551446A issued on Jul. 11, 2012 for "A Pillow is Provided With A Fan" (hereafter the "Chinese patent").

The Shaffer patent discloses an inflatable face down tanning and massage pad. The patent discloses:

"A support cushion for face down tanning or massage. The cushion is composed of inflatable plastic or rubber material, or solid foam material, and has an elongated recess for accommodating a person's face. Ventilation apertures extend from each side of the cushion and communicates with the recess to provide a constant fresh air supply."

Referring to Column 4 beginning on Line 35 through 55 the patent states:

"As can be readily seen in FIGS. 3 and 4, the recess 6 is dimensioned and configured to receive and engage the user's face F. A pair of substantially triangular-shaped side walls 20 extend along apposite sides of cushion 2. Ventilation apertures 8 extend from each side wall 20 of the cushion 2 and interconnect with the recess 6 as shown in FIG. 4. Communication between the aperture 8 and the recess 6 provides the user a continuous supply of fresh air, so that normal breathing may be maintained. An end wall 22 and a bottom wall 24 complete the hollow cushion 2.

The cushion 2 is made of plastic or rubber material, which can be inflated and hold pressure. The material is chosen for comfort. The cushion is sized so that it is convenient to carry it from place to place. In addition, when the cushion 2 is deflated, the user P is able easily to store the cushion 2, because the deflated cushion 2 requires only minimum storage space. The inflation mechanism (not shown) can be selected from various types of inflation mechanism well known to one in the art, such as an orally inflatable mechanism."

The Goldstein patent is a head support pad with air access conduit.

The patent discloses:

"A support pad or pillow for supporting the head in a face down, prone position, the pad having a face recess providing a breathing void and at least one air flow conduit extending from the face recess through the body of the support pad to the exterior to provide fresh ambient air to the face recess area, where the air flow conduit contains rigid support means to prevent the conduit from being compressed, restricted or closed by the weight of the user's head, and a filter to block particulate matter from entering the air flow conduit."

The Turner patent discloses:

"A pillow for supporting the head of user when the user is laying on their stomach. The pillow includes a body member defining an annular bore whereby the body member is substantially toroidal shaped. The body member is designed for supporting the head of the user whereby the annular bore is for receiving a face of the user when the user is laying face down. The body member has a plurality of ventilating bores extending through the body member. Each of the ventilating bores extends into the annular bore whereby the ventilating bores are designed for permitting air to flow to the user when the face of the user is positioned in the annular bore."

The Little patent is a Pillow With Air Filter. Referring to Column 2 beginning on Line 60 the patent states:

"FIG. 1 is a perspective view, FIG. 2 is a top view, and FIG. 3 is a front elevation view of the pillow with air filter 100, in accordance with a first exemplary embodiment of the pillow. The pillow with air filter 100, in accordance with the first embodiment, has a U-shape body comprising a back portion 102, a right arm portion 104, and a left arm portion 106. A right chamber 108 runs through the right arm portion 104 with a right intake opening 110 on a bottom exterior surface 112 and a right outflow opening 114 on a top exterior surface 116. Correspondingly, a left chamber 118 runs through the left arm portion 106 with a left intake opening 120 on the bottom exterior surface 112 and a left outflow opening 122 on the top exterior surface 116. Air filters are located in the left chamber 118 and right chamber 108. The air filters receive a flow of air from the intake openings 110 and 120, filter the air within the chambers 108 and 118, and supply cleansed air out of the outflow openings 114 and 122. Exemplary embodiments of the air filters are shown in FIGS. 6 10 and described in greater detail later in the specification."

Also, FIG. 6 discloses:

"FIG. 6 is a front, cross-sectional view of the pillow with air filter 100, in accordance with a first exemplary embodiment of the air filter. The left chamber 118 and the right chamber 108 run through the pillow. In each chamber 108, 118 a fan 602 can be positioned to draw air through the chambers 108, 118. Air is drawn in the intake openings 110, 120 of the chambers 108, 118 and blown out of the outflow openings 114, 122. The air filters shown in FIG. 6 are electrostatic precipitator filters 604. Electrostatic precipitator filters 604 can use an ion generator 606 to inject ions into the stream of air. The negatively charged ions cause the foreign particles in the air, i.e. dust, pollen, germs, and smoke particles, to become negatively charged in an ionization process. The air stream passes by positively charged plates 608. The charge plates 608 lay in a plane parallel to the air stream and perpendicular to the view of FIG. 6. The foreign particles, now negatively charged, are pulled towards the charge plates 608 and magnetically attach to the charge plates 608. The cleaned air stream, with foreign particles removed, flows out of the outflow openings 114, 122 of the chambers 108, 118. The outflow openings 114, 122 of the chambers 108, 118 can be positioned on the exterior surface of the pillow in a direction to facilitate the user breathing in the cleaned air. As discussed in the first and second exemplary embodiment, the outflow openings are located on the top surfaces pointing in a direction that directs the air to the front of the nose and mouth of the user. Of course, the outflow openings may be located in a different location on the pillow with air filter 100."

Claim 27 which is very broad reads:

"A pillow, comprising: a pillow body with a soft material; a chamber though the pillow body, the chamber having an interior, an intake opening, and an outflow opening; a fan positioned in the interior, the fan drawing air through the intake opening and into the interior and blowing the air out of the outflow opening; and an ion generator positioned in the interior to inject ions into the air."

The Silva patent discloses:

"The present invention provides a system for a gas delivery and monitoring system for delivering a gas product to a patient and receiving a gas product exhaled from a patient. In an embodiment, the gas delivery and monitoring system includes a head support made of resilient material and having therein a facial cavity. The facial cavity is configured to fit the contours of a patient's face and provides an oxygen rich environment for the patient while undergoing a medical procedure. In an embodiment, the facial cavity is shaped substantially in the form of a figure eight. In an embodiment, the facial cavity is further provided with one or more segmented edges that can be removed to further shape the facial cavity to the contours of the patient's face. In an embodiment, tubing is used to deliver oxygen from an oxygen source to the patient. Similarly, tubing is also used to receive carbon dioxide exhaled by the patient so that it might be measured by a carbon dioxide monitor. Still further, an aperture extending from the facial cavity to an outer surface of the head support may be provided as a conduit for the gas products. In yet another embodiment, the tubes may be located within the aperture."

The Wallis patent discloses a cushion with a scent cartridge. The patent discloses:

"A cushion device comprising a body having an outer surface defining a boundary and at least one cartridge positioned outside the boundary. The cartridge may include a scented substance and a cover for varying the exposure of it to the surroundings."

The Albu Published patent application discloses:

"The present invention relates to a an active pillow system and a method for manipulating a person's resting conditions, wherein the actual resting conditions of the person are determined by a sensor unit, an actigraph, a temperature sensor and/or a humidity sensor for instance, and wherein an acoustic synthetic jet cooling mechanism, is triggered by the determined actual resting conditions for manipulating the person's resting conditions."

The focus of the patent is best described in Section 0011 which reads as follows:

"[0011] The acoustic synthetic jet cooling mechanism comprises a diaphragm pump and particularly a loudspeaker, for instance. It is a great advantage of the active pillow system that the acoustic synthetic jet cooling mechanism is able to generate a strong airflow on the one hand, but it does not require a fast rotational movement of a rotor on the other hand. Therefore, aerodynamic noise, vibrations, abrasions and grinding noises caused by the moving rotor can be avoided. This is very important as the active pillow system is provided to improve the person's resting or sleeping conditions and must not be a disturbance source for the resting or sleeping person. In particular, if the person's head lies on the pillow typically with a small distance to the air conditioner. In this active pillow system the air conditioner consists of a loudspeaker in a chamber through a special construction in the chamber a by applying certain frequencies an airjet is produced that can be used to cool devices. It is shown that the acoustic synthetic jet cooling method allows miniaturization, it is very reliable because it has only one moving part that is frictionless driven by a magnetic field. This in contrast to other cooling based methods based on water such as pumps or airflow such as fans. The term "resting" in the sense of the present inventions includes relaxing, as well as sleeping, recovering, regeneration and/or rehabilitation of the person. The wording "pillow" can be understood as a head cushion, a mattress, a sofa cushion, a blanket, a seat cover or the like. Preferably, the acoustic synthetic jet cooling mechanism comprises a membrane which is operated by an electromagnetic and/or a piezoelectric driver."

The Wang Chinese patent abstract reads as follows:

"The utility model relates to a cool pillow. The existing cool pillows, such as bamboo cool pillows, bine cool pillows, etc. All have the problems of bad ventilation property, slow heat dispersion, etc. As for the utility model, a miniature electric fan is installed under the pillow surface, the pillow surface is also bored with ventilating holes, and the breeze generated by the miniature electric fan can be blown out through the ventilating holes. The utility model has the advantages of good ventilation property and heat dispersion, comfortable and cool rest feelings, etc."

The disclosure reads as follows:

"The purpose of the utility model is to provide a good air permeability, the cool pillow of the breeze can be produced.

The solution of the utility model: in cool pillow under surface of a miniature electric fan, vent holes are drilled on the pillow, the miniature electric fan is blown out through the vent, the comfort is produced.

FIG. 1 is the schematic diagram of the structure of the utility model.

FIG. 2 is the A-A sectional view of the utility model.

Combined with the Figure below the utility model relates to the detailed description:

Pillow surface 3 and the beam 8 mounted on two pillow foot 1 is, of the pillow is 3 is drilled with the air hole 2, the pillow surface 3 with a minitype electric fan below, the miniature electric fan motor 4 and the vane 6 composition. Pillow surface 3 is fixed with the inner side of the blade shroud 7, blade shroud 7 covers the blade 6. Pillow foot 7 is also provided with the inner side of the two side plates 5. When in use, 220V commercial power obtained by the DC regulated power supply 12V direct current (or directly using the dry battery obtain 12V direct current) to drive the miniature motor 4, so as to drive the blade 6 rotation, generate breeze. Breeze motor 4 to the incoming line is provided with switch K, so that the person lying down at any time when the power supply is cut off according to requirements.

The utility model has air permeability, good heat dissipation, comfortable pillow feeling, cool, and the like.

Embodiment

The 3 is drilled with 13 row 30 row air hole 2, the 3 lower beam 8 is provided with two miniature motor 4, miniature motor 4 are respectively provided with a vane 6, each blade 6 are covered with a blade shroud 7, two blade shroud 7 is fixed on the surface 3 of the inner side. Two pillow foot 1 slant at the inner side of the two side plates 5."

The Korean Patent No. KR10125713 English abstract reads:

"PURPOSE: A ventilation pillow is provided, which is capable of inducing natural sleep and sound sleep in the hot summer or rainy season. CONSTITUTION: A ventilation pillow comprises: a liner(10); a ventilation tube (30) which is opened to both sides of the pillow and in which a ventilation hole is formed in the external periphery; and an inner container(40) in which a fan discharging the air of the pillow to the outside is installed. The liner comprises a plurality of compartments which are divided by a partition wall radially. Each compartment is filled with each different fillers."

The Chinese Patent No. CN102551446A English abstract reads as follows:

"A pillow is provided with a fan, characterized in that the fan has a fan assembly, in its inside, with a fan board of the fan assembly, the fan support is provided with at least one fan, the fan frame is also provided with a to the fan power supply charging the battery, the surface of the pillow with a is electrically connected with the rechargeable battery charging interface, also has the advantages of the vent towards the fan, the said vents covered by the web, between the vent and the fan is in a hollow structure, the present invention is provided with a fan of the pillow, can use hot in summer days, so as to utilize the fan to blow cool air on the pillow Oudan, the head of a person is avoided a large amount of sweat, on the one hand so that the role of the users can obtain the cool, on the other hand will also avoid sweat permeation pillow, form a peculiar smell."

The present inventor is also the inventor of two design patents, Patent D655,559 for a pillow which is rectangular in shape and a Patent D656,356 which has an arcuate rounded front. Bob disclose a cavity for resting a person's face and air channels to provide breathing air to the cavity.

There is a significant need for an improved pillow which is an improvement over the prior art known to the present inventor and also over the inventor's two designs patents discussed above.

SUMMARY OF THE INVENTION

The present invention is an innovative pillow which contains openings for a person to place their face as well as side openings which enable air to enter the cavity so that the person can breathe. The device contains a fan which blows air into the cavity of the pillow so that a person can have cooling air while their face is in the pillow. The device can also be impregnated with essential oils such as eucalyptus so that the various beneficial therapeutic effects can be blown into a person's face while they rest their face within the pillow.

It is an object of the present invention to create a pillow comprising (a) an upper surface, a lower surface and an exterior sidewall retained together to form the outer shape of the pillow, the upper surface, lower surface and sidewall are formed in one piece and are retained together by fastening means, the upper surface, lower surface and exterior sidewall surround a pillow chamber into which cushioning material is retained; (b) a facial cavity extending from the upper surface to an interior of the lower surface, the facial cavity surrounded by an interior circumferential sidewall; (c) a first side air channel extending from a first side of the exterior sidewall, through the cushioning material, and through the interior circumferential sidewall into the facial cavity, a first exterior retaining ring retaining the opening of the first side air channel on the first exterior sidewall, a first interior retaining ring retaining the opening of the first side air channel on the first interior side of the interior circumferential sidewall; (d) a second side air channel extending from a second side of the exterior sidewall, through the cushioning material, and through the interior circumferential sidewall into the facial cavity, a second exterior retaining ring retaining the opening of the second side air channel on the second exterior sidewall, a second interior retaining ring retaining the opening of the second side air channel on the second interior side of the interior circumferential sidewall; (e) the pillow is slanted so that a rear sidewall of the pillow is taller than a front sidewall of the pillow; (f) an air-fan air channel extending from the rear sidewall into a rear interior sidewall of the interior circumferential sidewall; (g) an air-fan housing supporting an air-fan having rotating blades which rotate around a central shaft, the air-fan blades are driven by an air-fan driving means, an air-fan housing having a pair of oppositely disposed walls with a space between them and a rear wall which supports the air-fan blades which blows air through the open space between the air-fan housing walls; (h) a scent retaining means located within the open space between the housing walls, the scent retaining means including a housing having a front wall and a pair of sidewalls which support a horizontal shelf, a rear of the housing is open, the housing supports a scent retaining member to which scent is applied, the scent retaining member is placed on the shelf and supported between the sidewalls and front wall and housing, the housing sidewalls are press fit retained between an interior surface of each of the air-fan housing walls so that the scent retaining member faces the fan blades; and (i) the air-fan assembly is press fit retained within the air-fan air channel so that the fan blades blow air into the facial cavity and the rear wall of the air-fan housing is flush with the rear sidewall of the pillow and when the air-fan is turned on, the fan blades rotate and blow air over the scent retaining member so that the scent is blown into the facial cavity to provide a relaxing and sensual experience to a person whose face is resting within the facial cavity.

It is further object of the present invention to create a pillow comprising: A pillow comprising: (a) an upper surface, a lower surface and an exterior sidewall retained together to form the outer shape of the pillow, the upper surface, lower surface and sidewall are formed in one piece and are retained together by fastening means, the upper surface, lower surface and exterior sidewall surround a pillow chamber into which cushioning material is retained; (b) a facial cavity extending from the upper surface to an interior of the lower surface, the facial cavity surrounded by an interior circumferential sidewall; (c) a first side air channel extending from a first side of the exterior sidewall, through the cushioning material, and through the interior circumferential sidewall into the facial cavity; (d) a second side air channel extending from a second side of the exterior sidewall, through the cushioning material, and through the interior circumferential sidewall into the facial cavity; (e) an air-fan air channel extends from a location on the sidewall into the interior circumferential sidewall; (f) an air-fan housing supporting an air-fan having rotating blades which rotate around a central shaft the air-fan blades are driven by an air-fan driving means, pair of oppositely disposed walls with a space between them and a rear wall which supports the fan blades which blows air through the space between the air-fan housing walls; (g) a scent retaining means located within the space between the air-fan housing walls including a scent retaining member in an airflow path of the air-fan blades; and (h) the air-fan housing is press fit retained within the air-fan air channel so that the fan blades blow air into the facial cavity with airflow causing scent from the scent retaining member to be blown into the facial cavity to provide a relaxing and sensual experience to a person whose face is resting within the facial cavity.

It is an additional object of the present invention to create a pillow comprising: (a) an upper surface, a lower surface and an exterior sidewall retained together to form the outer shape of the pillow, the upper surface, lower surface and sidewall are formed in one piece and are retained together by fastening means, the upper surface, lower surface and exterior sidewall surround a pillow chamber into which cushioning material is retained; (b) a facial cavity extending from the upper surface to an interior of the lower surface, the facial cavity surrounded by an interior circumferential sidewall; (c) at least one air channel extending from a first side of the exterior sidewall, through the cushioning material, and through the interior circumferential sidewall into the facial cavity; (d) an air-fan air channel extending from a location on the sidewall into the interior circumferential sidewall; (e) an air-fan housing supporting an air-fan having rotating blades which rotate around a central shaft, the air-fan blades are driven by an air-fan driving means, a pair of oppositely disposed walls with a space between them and a rear wall which supports the fan blades which blows air through the space between the air-fan housing walls; (f) a scent retaining means located within the space between the air-fan housing walls including a scent retaining member in an airflow path of the air-fan blades; and (g) the air-fan housing is within the air-fan air channel so that the fan blades blow air into the facial cavity with airflow causing scent from the scent retaining member to be blown into the facial cavity.

Further, it is an object of the present invention to create a pillow comprising: (a) an exterior surface including at least an upper surface and an exterior sidewall with cushioning material bounded by the upper surface and exterior sidewall; (b) a facial cavity extending from the upper surface into the cushioning material, the facial cavity surrounded by an interior circumferential sidewall; (c) at least one air channel extending from the exterior sidewall, through the cushioning material, and through the interior circumferential sidewall terminating at the facial cavity; (d) an air-fan air channel extending from a location on the sidewall into the interior circumferential sidewall; (e) an air-fan housing supporting an air-fan driven by air-fan driving means, the air-fan blowing air through the air-fan housing; (f) a scent retaining means located within the air-fan housing including a scent retaining member in an airflow path of the air-fan; and (g) the air-fan housing is retained within the air-fan air channel so that the air-fan blows air into the facial cavity with airflow causing scent from the scent retaining member to be blown into the facial cavity.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Figure 1:
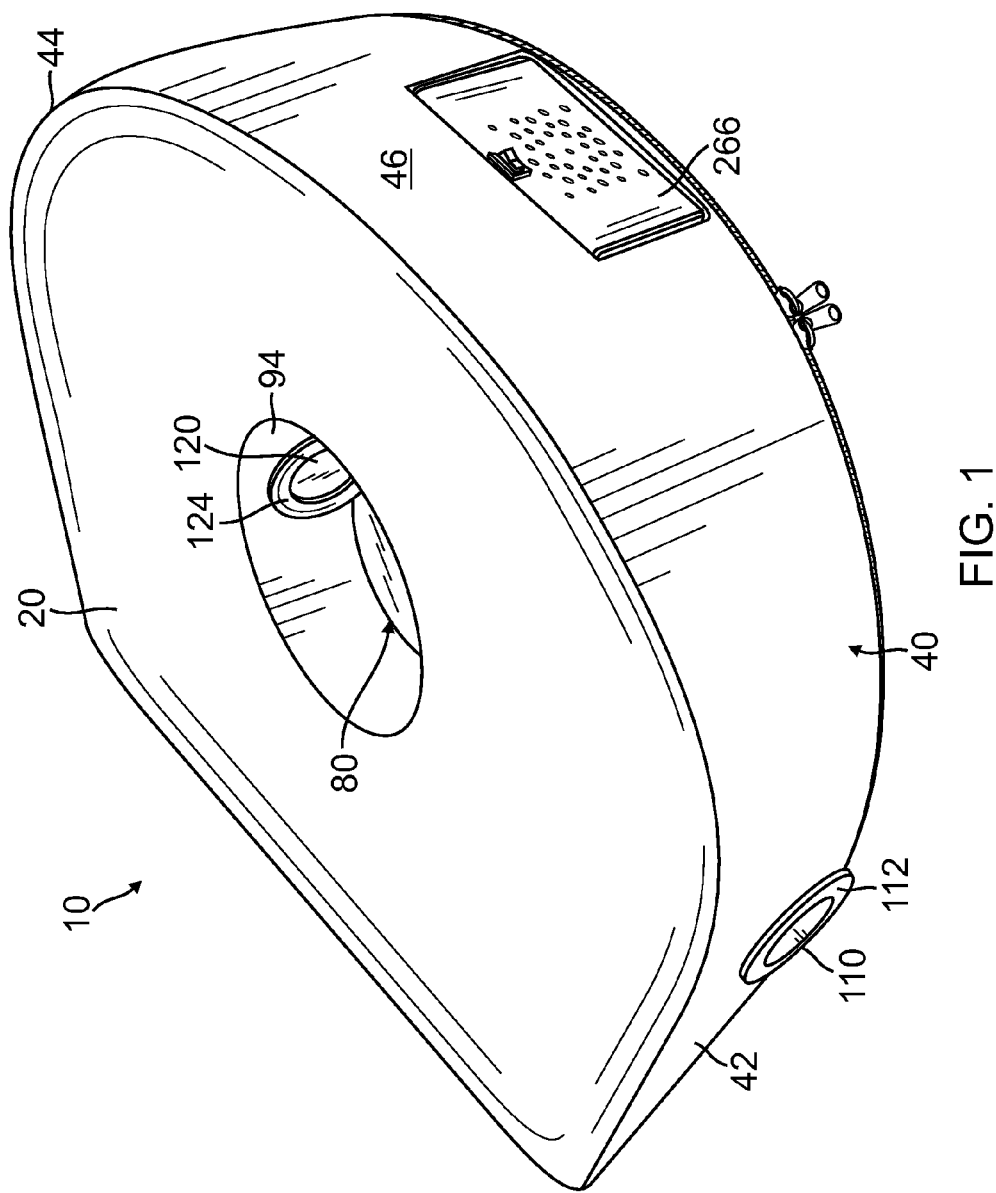
FIG. 1 is a top perspective view of the present invention pillow with a facial cavity, breathing air channels leading to the facial cavity and a fan to blow air and scented oils into the facial cavity.
Figure 2:
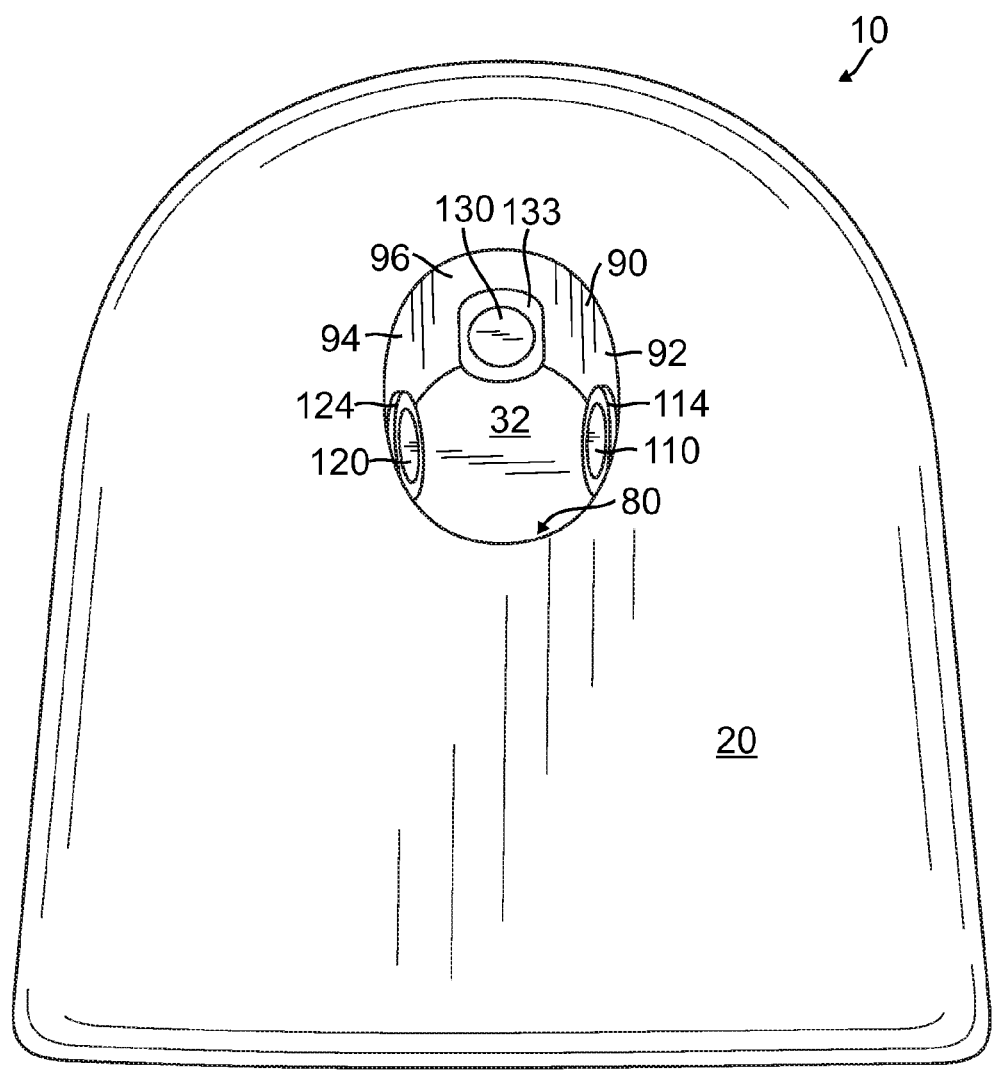
FIG. 2 is a top elevational view of the present invention pillow with a facial cavity, breathing air channels leading to the facial cavity and a fan to blow air and scented oils into the facial cavity.
Figure 3:
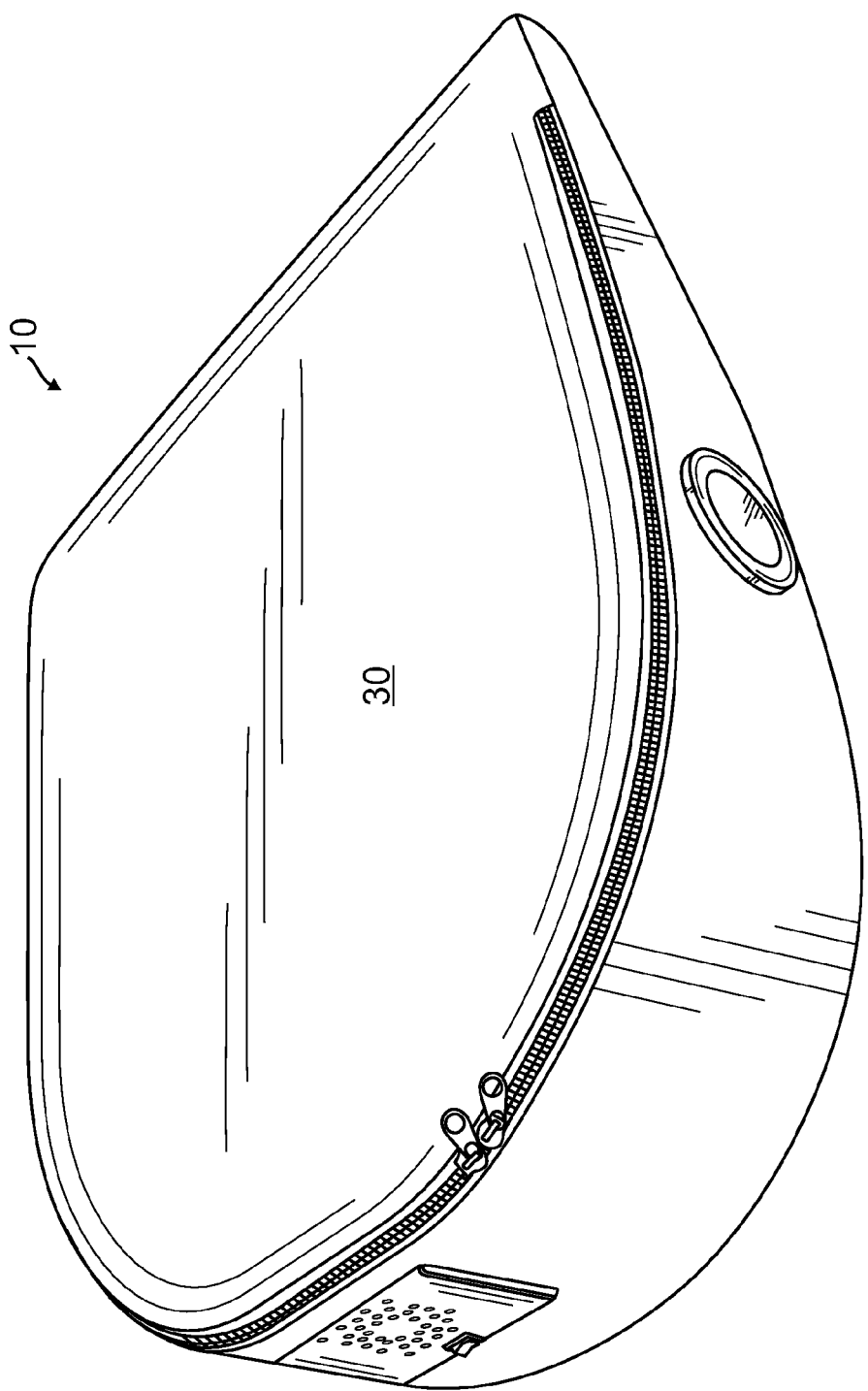
FIG. 3 is a bottom rear perspective view of the present invention pillow with a facial cavity, breathing air channels leading to the facial cavity and a fan to blow air and scented oils into the facial cavity.

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Referring to FIGS. 1 through 3 and 7, the present invention pillow 10 has an upper surface 20, a lower surface 30 and an exterior sidewall 40 retained together to form the outer shape of the pillow 10. The upper surface, lower surface and sidewall are made from material selected from the group consisting of vinyl, polyvinyl, plastic, and leather. In a preferred embodiment, the upper surface 20, lower surface 30 and sidewall 40 are formed in one piece and are retained together by fastening means such as a zipper 50. In addition to the closing means such as a zipper, the closing means can include closing means selected from the group consisting of one zipper, two zippers, mating hook and loop fasteners and mating snap fasteners. The upper surface 20, lower surface 30 and exterior sidewall 40 surround a pillow chamber 60 into which cushioning material such as foam 70 is retained. The upper surface 20, lower surface 30 and exterior sidewall 40 are made of washable material such as vinyl so that they can be removed from the foam interior 70 and washed and cleaned.

The pillow 10 has a facial cavity 80 extending from the top surface 20 to an interior 32 of lower surface 30, the chamber surrounded by an interior circumferential sidewall 90. The interior circumferential sidewall 90 can be formed as part of the upper surface 20 or a separate unit.

A first side air channel 110 extends from a first side 42 of exterior sidewall 40, through the foam interior 70 and through the interior circumferential sidewall 90 into the facial cavity 80. A first exterior retaining ring 112 retains the opening of the first side air channel on the first exterior side 42. A first interior retaining ring 114 retains the opening of the first side air channel 110 on the first interior side 92 of the interior circumferential sidewall 90.

A second side air channel 120 extends from a second side 44 of exterior sidewall 40, through the foam interior 70 and through the interior circumferential sidewall 90 into the facial cavity 80. A second exterior retaining ring (not shown but comparable to retaining ring 112A) retains the opening of the second side air channel on the second exterior side 44. A second interior retaining ring 124 retains the opening of the second side air channel 120 on the second interior side 94 of the interior circumferential sidewall 90.

Therefore, through air channels 110 and 120, breathing air can be breathed into the facial cavity 80 and exhaled from the facial cavity 80.

Figure 8:
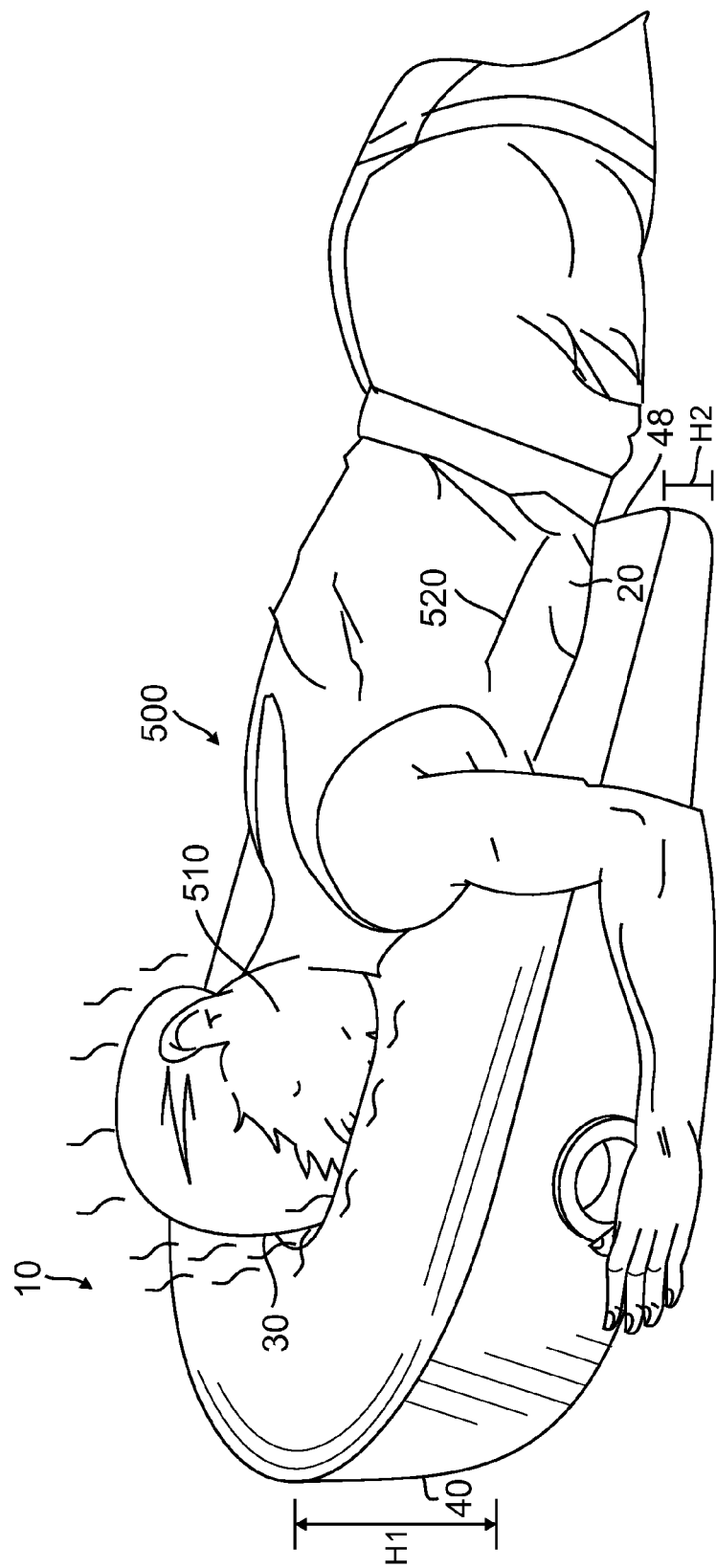
FIG. 8 is a perspective view of a person with the person's face in the cavity of the present invention, the person's upper torso lying on the upper surface of the present invention.

As best illustrated in FIG. 8, the pillow 10 is slanted, being taller with a height of "H1" at its rear sidewall 46 and at a lower height "H2" at its front sidewall 48, the slant enabling a person 500 to place the person's face 510 into the facial cavity 80, with the upper torso 520 resting on the upper surface 20.

The key innovation of the present invention is the incorporation of a fan blowing air into the facial cavity, and a scent retaining means in the path of air blown by the fan so that scent such as essential oils are also blown into the facial cavity 80.

An air fan air channel 130 extends from rear sidewall 46 into rear interior sidewall 96 of interior circumferential sidewall 90, where it is supported by an interior retaining ring 132.

Figure 4:
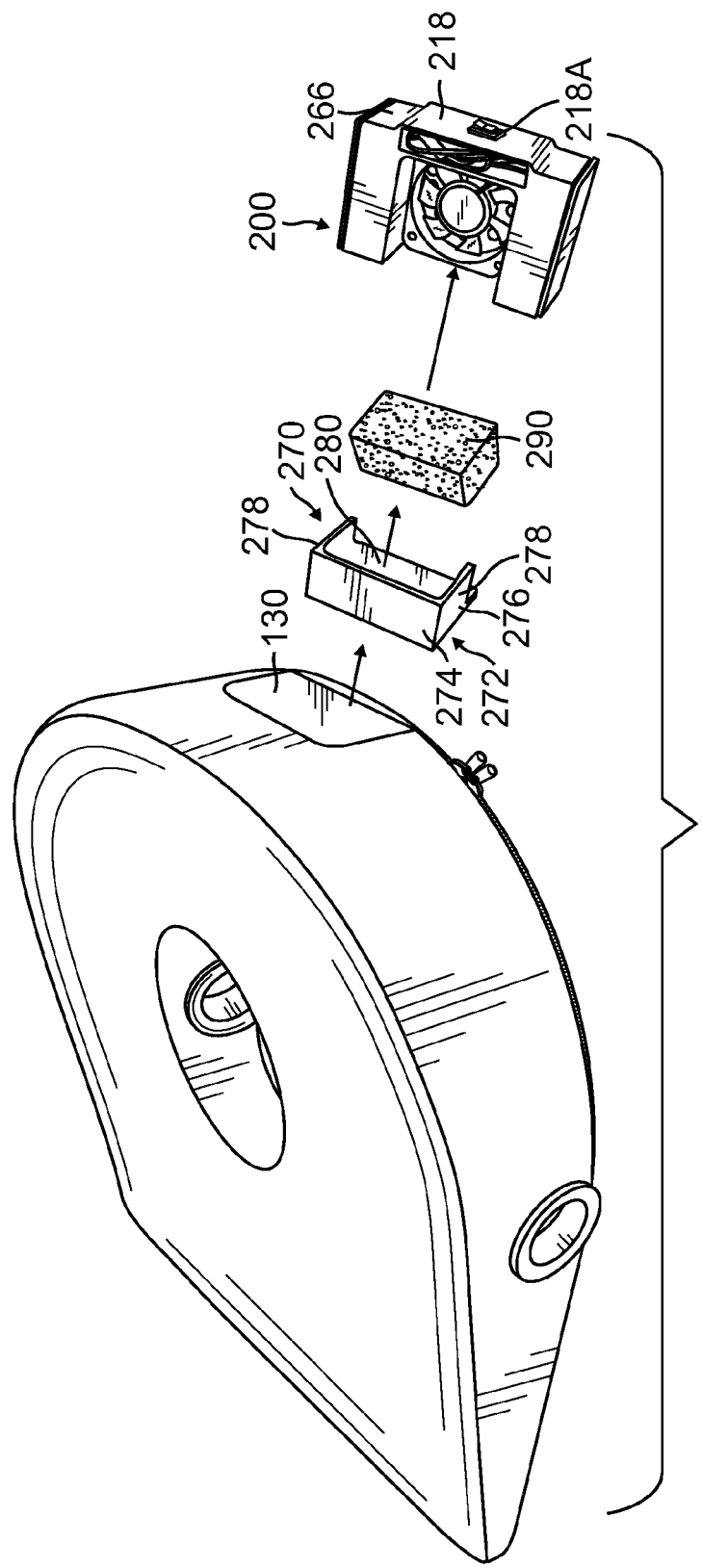
FIG. 4 is an exploded perspective view of the present invention pillow with a facial cavity, breathing air channels leading to the facial cavity and a fan to blow air and scented oils into the facial cavity, the components of the fan and scent retaining apparatus shown in the exploded view.
Figure 5:
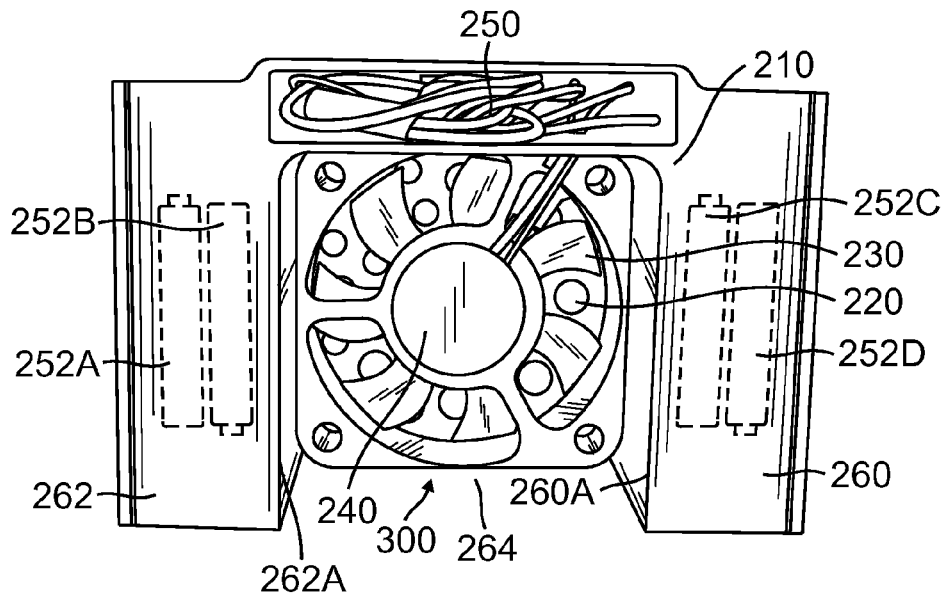
FIG. 5 is a front elevational view of the fan assembly of the present invention.
Figure 6:
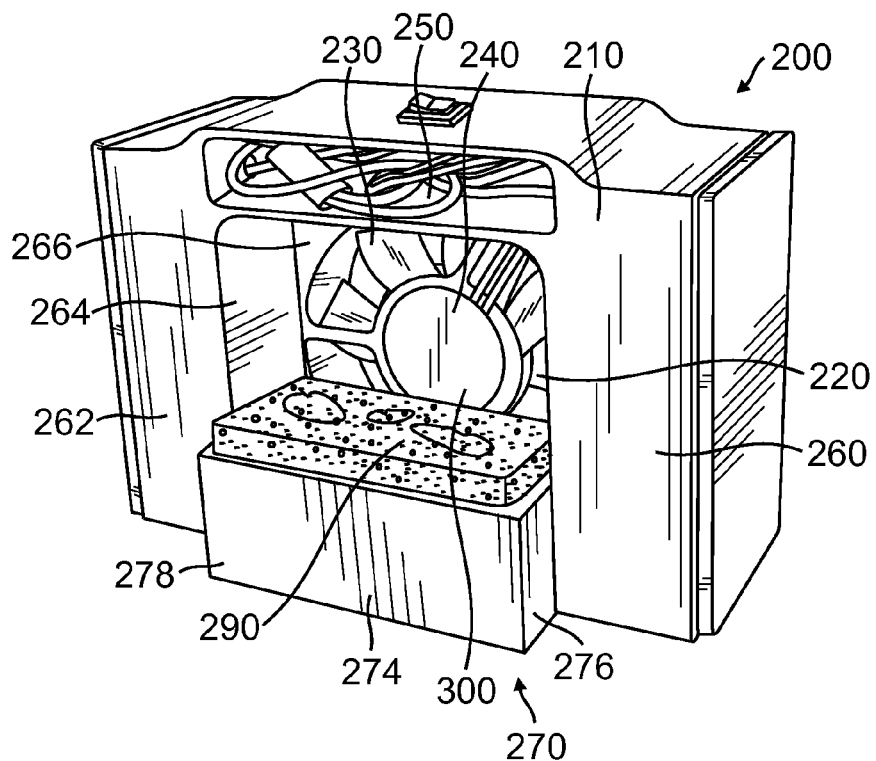
FIG. 6 is a front perspective view of the fan assembly and scent and oil retaining apparatus of the present invention.
Figure 7:
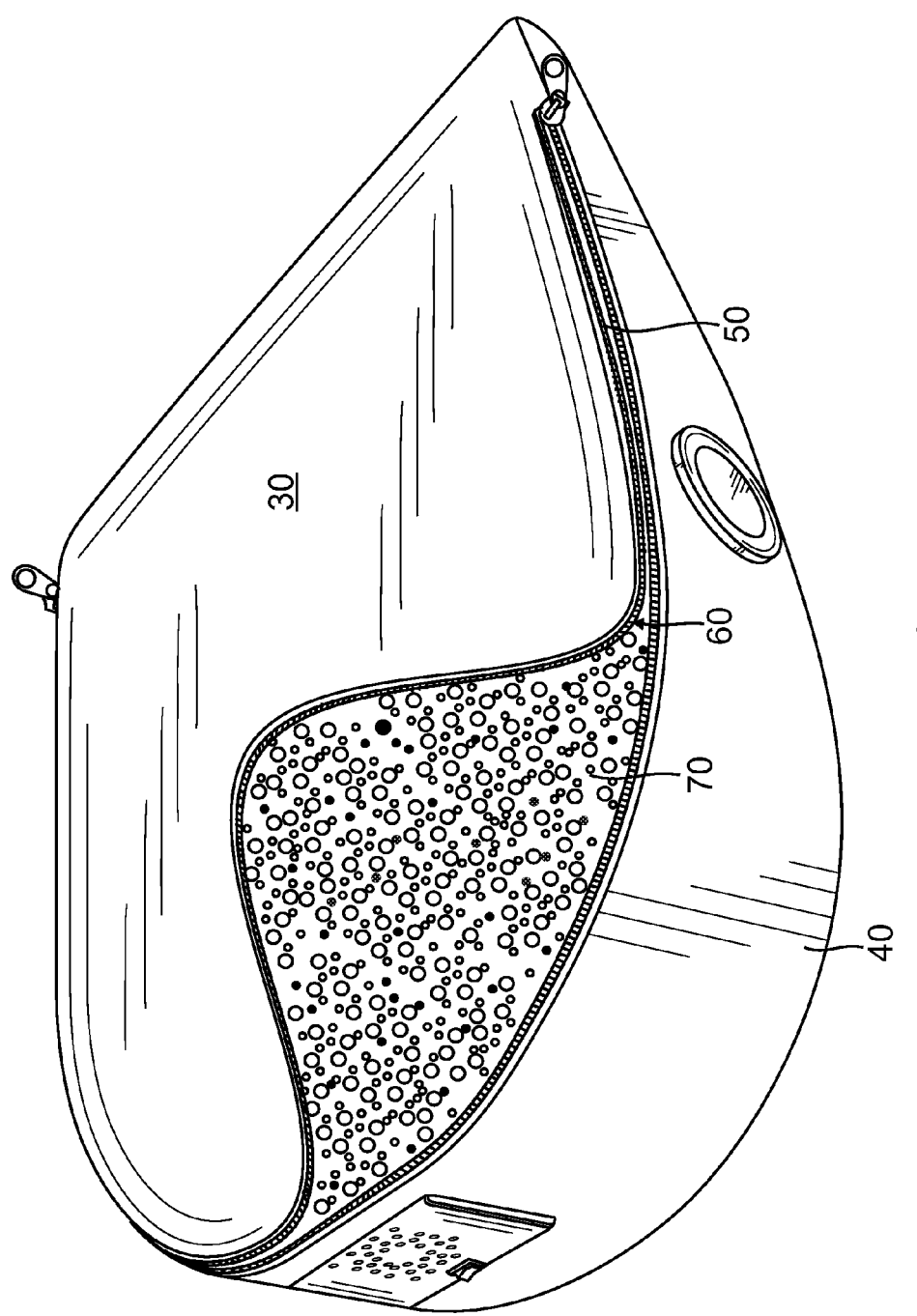
FIG. 7 is a bottom rear perspective view of the present invention pillow with a facial cavity, breathing air channels leading to the facial cavity and a fan to blow air and scented oils into the facial cavity, the rear cover partially pulled away to disclose the interior cushioning foam.

Referring to FIGS. 4 through 6, the air-fan assembly 200 is illustrated. An air-fan housing 210 supports an air-fan 220 having rotating blades 230 which rotate around a central shaft 240. The air-fan blades 220 are driven by conventional fan driving means such an electric motor which is driven by either electric power such as 120 volts and/or by battery power through a multiplicity of batteries. The electric wire 250 is illustrated. The batteries 252A, 252B, 252C and 252D are shown in dotted lines in the housing. It will be appreciated that the fan blades 220 are driven by a conventional electric circuit connected to a battery, the circuit connected to the source of power and including an on/off switch 218A at the rear 218 of the air-fan housing 210. The air-fan housing 210 has a pair of oppositely disposed walls 260 and 262 with a space 264 between them. The rear wall 266 supports the air-fan 220 and fan blades 230 which blows air through the open space 264 between the air-fan housing walls 262 and 264.

A scent retaining means 270 is located with the open space 264 between the housing walls 260 and 262. In one embodiment, the scent retaining means 270 includes a housing 272 having a front wall 274 and a pair of sidewalls 276 and 278 which support a horizontal shelf 280. The rear of the housing 282 is open. The housing supports a scent retaining member 290 which by way of example is a sponge. The scent retaining member 290 is either dipped in scent or essential oils or a bottle retaining the scent or essential oil causes a few drops to be applied to the sponge so that the sponge retains the scent or essential oil. The scent or essential oil can be one or more of any multiplicity of such scents or essential oils such as eucalyptus, lavender, rosemary, hemp, peppermint, etc. The scent retaining member 290 is placed on the shelf 280 and supported between the sidewalls 276 and 278 and front wall 274 and housing 272. The housing sidewalls 276 and 278 are press fit retained between interior surface 260A of housing all 260 and the interior surface 262A of housing wall 262 so that the scent retaining member 290 faces the fan blades 230.

The air-fan assembly 200 is press fit retained within the air-fan air channel 130 so that the fan blades 230 blades blow air 300 into the facial cavity 80 and the rear wall 266 is flush the rear sidewall 46.

The scent is selected from the group consisting of fragrances and essential oils.

When the air-fan is turned on, either by turning the electric switch 218A on so that batteries 252A, 252B, 252C and 252D energize th motor or is pugged into a 120 volt circuit (either directly or through a transformer which reduces the 120 volt current to run a low voltage motor, the fan blades 230 rotate and blow air 300 over the scent retaining member 290 so that the scent and/or essential oils is blown into the facial cavity to provide a relaxing and sensual experience to a person 500 whose face 510 is resting within the cavity. As a result, the present invention pillow provides a therapeutic effect as well as an enjoyable relaxing experience.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. A pillow comprising:
   a. an upper surface, a lower surface and an exterior sidewall retained together to form the outer shape of the pillow, the upper surface, lower surface and sidewall are formed in one piece and are retained together by fastening means, the upper surface, lower surface and exterior sidewall surround a pillow chamber into which cushioning material is retained;
   b. a facial cavity extending from the upper surface to an interior of the lower surface, the facial cavity surrounded by an interior circumferential sidewall;
   c. a first side air channel extending from a first side of the exterior sidewall, through the cushioning material, and through the interior circumferential sidewall into the facial cavity, a first exterior retaining ring retaining the opening of the first side air channel on the first exterior sidewall, a first interior retaining ring retaining the opening of the first side air channel on the first interior side of the interior circumferential sidewall;
   d. a second side air channel extending from a second side of the exterior sidewall, through the cushioning material, and through the interior circumferential sidewall into the facial cavity, a second exterior retaining ring retaining the opening of the second side air channel on the second exterior sidewall, a second interior retaining ring retaining the opening of the second side air channel on the second interior side of the interior circumferential sidewall;

e. the pillow is slanted so that a rear sidewall of the pillow is taller than a front sidewall of the pillow;

f. an air-fan air channel extending from the rear sidewall into a rear interior sidewall of the interior circumferential sidewall;

g. an air-fan housing supporting an air-fan having rotating blades which rotate around a central shaft, the air-fan blades are driven by an air-fan driving means, the air-fan housing having a pair of oppositely disposed walls with a space between them and a rear wall which supports the air-fan blades which blows air through the open space between the air-fan housing walls;

h. a scent retaining means located within the open space between the housing walls, the scent retaining means including a housing having a front wall and a pair of sidewalls which support a horizontal shelf, a rear of the housing is open, the housing supports a scent retaining member to which scent is applied, the scent retaining member is placed on the shelf and supported between the sidewalls and front wall and housing, the housing sidewalls are press fit retained between an interior surface of each of the air-fan housing walls so that the scent retaining member faces the fan blades; and i. the air-fan assembly is press fit retained within the air-fan air channel and the rear wall of the air-fan hosing is flush with the rear sidewall of the pillow so that the fan blades blow air into the facial cavity and the airflow is encapsulated into the facial cavity, and when the air-fan is turned on, the fan blades rotate and blow air over the scent retaining member so that the entire airflow scent is entirely blown into the facial cavity and onto a face of a person whose face is resting within the facial cavity to provide a relaxing and sensual experience to the person whose face is resting within the facial cavity.

2. The pillow in accordance with claim 1, further comprising: said upper surface, said lower surface and said sidewall are made from material selected from the group consisting of vinyl, polyvinyl, plastic, and leather.

3. The pillow in accordance with claim 1, further comprising; said cushioning material is made of foam.

4. The pillow in accordance with claim 1, further comprising: said closing means is selected from the group consisting of at least one zipper, two zippers, mating hook and loop fasteners, and mating snap fasteners.

5. The pillow in accordance with claim 1, further comprising: the scent is selected from the group consisting of fragrances and essential oils.

6. A pillow comprising:

a. an upper surface, a lower surface and an exterior sidewall retained together to form the outer shape of the pillow, the upper surface, lower surface and sidewall are formed in one piece and are retained together by fastening means, the upper surface, lower surface and exterior sidewall surround a pillow chamber into which cushioning material is retained;

b. a facial cavity extending from the upper surface to an interior of the lower surface, the facial cavity surrounded by an interior circumferential sidewall;

c. a first side air channel extending from a first side of the exterior sidewall, through the cushioning material, and through the interior circumferential sidewall into the facial cavity;

d. a second side air channel extending from a second side of the exterior sidewall, through the cushioning material, and through the interior circumferential sidewall into the facial cavity;

e. an air-fan air channel extends from a location on the sidewall into the interior circumferential sidewall;

f. an air-fan housing supporting an air-fan having rotating blades which rotate around a central shaft, the air-fan blades are driven by an air-fan driving means, pair of oppositely disposed walls with a space between them and a rear wall which supports the fan blades which blows air through the space between the air-fan housing walls;

g. a scent retaining means located within the space between the air-fan housing walls including a scent retaining member to which scent is applied, the scent retaining member is press fit retained in a housing which is press fit retained in the air-fan channel, the scent retaining member is also in an airflow path of the air-fan blades; and h. the air-fan housing is press fit retained within the air-fan air channel, the air fan housing having a rear wall which is flush with a rear sidewall of the pillow so that the fan blades blow air into the facial cavity and the airflow is encapsulated within the facial cavity with airflow causing scent from the scent retaining member to be entirely blown into the facial cavity and onto a face of a person whose face is resting within the facial cavity to provide a relaxing and sensual experience to the person whose face is resting within the facial cavity.

7. The pillow in accordance with claim 6, further comprising: said pillow is slanted so that a rear sidewall of the pillow is taller than a front sidewall of the pillow.

8. The pillow in accordance with claim 6, further comprising: said housing having a pair of oppositely disposed walls with a space between them and a rear wall which supports the air-fan blades which blows air through the space between the air-fan housing walls.

9. The pillow in accordance with claim 8, further comprising: said means including a housing having a front wall and a pair of sidewalls which support a horizontal shelf, a rear of the housing is open, the housing supports a scent retaining member to which scent is applied, the scent retaining member is placed on the shelf and supported between the sidewalls and front wall and housing, the housing sidewalls are press fit retained between an interior surface of each of the air-fan housing walls so that the scent retaining member faces the fan blades.

10. The pillow in accordance with claim 9, further comprising: said upper surface, said lower surface and said sidewall are made from material selected from the group consisting of vinyl, polyvinyl, plastic, and leather.

11. The pillow in accordance with claim 6, further comprising; said cushioning material is made of foam.

12. The pillow in accordance with claim 6, further comprising: the scent is selected from the group consisting of fragrances and essential oils.

13. A pillow comprising:

a. an upper surface, a lower surface and an exterior sidewall retained together to form the outer shape of the pillow, the upper surface, lower surface and sidewall are formed in one piece and are retained together by fastening means, the upper surface, lower surface and exterior sidewall surround a pillow chamber into which cushioning material is retained;

b. a facial cavity extending from the upper surface to an interior of the lower surface, the facial cavity surrounded by an interior circumferential sidewall;

c. at least one air channel extending from a first side of the exterior sidewall, through the cushioning material, and through the interior circumferential sidewall into the facial cavity;

d. an air-fan air channel extending from a location on the sidewall into the interior circumferential sidewall;

e. an air-fan housing supporting an air-fan having rotating blades which rotate around a central shaft, the air-fan blades are driven by an air-fan driving means, a pair of oppositely disposed walls with a space between them and a rear wall which supports the fan blades which blows air through the space between the air-fan housing walls;

f. a scent retaining means located within the space between the air-fan housing walls including a scent retaining member is retained in a housing which is press fit retained in the air-fan channel, the scent retaining member is in an airflow path of the air-fan blades; and g. the air-fan housing is within the air-fan air channel, the air fan housing having a rear wall which is flush with a sidewall of the pillow so that the fan blades blow air into the facial cavity and the airflow is encapsulated within the facial cavity with airflow causing scent from the scent retaining member to be entirely blown into the facial.

14. The pillow in accordance with claim 13, further comprising: said pillow is slanted so that a rear sidewall of the pillow is taller than a front sidewall of the pillow.

15. The pillow in accordance with claim 13, further comprising: said housing having a pair of oppositely disposed walls with a space between them and a rear wall which supports the air-fan blades which blows air through the space between the air-fan housing walls.

16. The pillow in accordance with claim 15, further comprising: said means including a housing having a front wall and a pair of sidewalls which support a horizontal shelf, a rear of the housing is open, the housing supports a scent retaining member to which scent is applied, the scent retaining member is placed on the shelf and supported between the sidewalls and front wall and housing, the housing sidewalls are press fit retained between an interior surface of each of the air-fan housing walls so that the scent retaining member faces the fan blades.

17. The pillow in accordance with claim 13, further comprising: said upper surface, said lower surface and id said sidewall are made from material selected from the group consisting of vinyl, polyvinyl, plastic, and leather.

18. The pillow in accordance with claim 13, further comprising; said cushioning material is made of foam.

19. The pillow in accordance with claim 13, further comprising: said closing means is selected from the group consisting of at least one zipper, two zippers, mating hook and loop fasteners, and mating snap fasteners.

20. A pillow comprising:

a. an exterior surface including at least an upper surface and an exterior sidewall with cushioning material bounded by the upper surface and exterior sidewall;

b. a facial cavity extending from the upper surface into the cushioning material, the facial cavity surrounded by an interior circumferential sidewall;

c. at least one air channel extending from the exterior sidewall, through the cushioning material, and through the interior circumferential sidewall terminating at the facial cavity;

d. an air-fan air channel extending from a location on the sidewall into the interior circumferential sidewall;

e. an air-fan housing supporting an air-fan driven by air-fan driving means, the air-fan blowing air through the air-fan housing;

f. a scent retaining means located within the air-fan housing including a scent retaining member retained in a housing which is press fit retained in the air flow channel, the scent retaining member is in an airflow path of the air-fan; and g. the air-fan housing is retained within the air-fan air channel, the air fan housing having a rear wall which is flush with a sidewall of the pillow so that the air-fan blows air into the facial cavity and the airflow is encapsulated within the facial cavity with airflow causing scent from the scent retaining member to be entirely blown into the facial cavity.

\* \* \* \* \*